United States Patent
Wu et al.

(10) Patent No.: US 8,557,756 B2
(45) Date of Patent: Oct. 15, 2013

(54) COMPATIBLE MIXTURES OF ANIONIC AND CATIONIC SURFACTANTS

(75) Inventors: Yongfu Wu, Rolla, MO (US); Cynthia L. Rand, Sanford, MI (US); Wanglin Yu, Pearland, TX (US); Irina V. Graf, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 219 days.

(21) Appl. No.: 13/160,623

(22) Filed: Jun. 15, 2011

(65) Prior Publication Data

US 2011/0319313 A1   Dec. 29, 2011

Related U.S. Application Data

(60) Provisional application No. 61/359,403, filed on Jun. 29, 2010.

(51) Int. Cl.
C11D 1/65   (2006.01)

(52) U.S. Cl.
USPC ........... 510/123; 510/119; 510/125; 564/295; 562/101; 562/110

(58) Field of Classification Search
USPC ........... 510/119, 123, 125; 564/295; 562/101, 562/110
See application file for complete search history.

(56) References Cited

U.S. PATENT DOCUMENTS

| | | | |
|---|---|---|---|
| 3,637,565 A | 1/1972 | Sheetz | |
| 3,668,136 A | 6/1972 | Barker | |
| 4,255,294 A | 3/1981 | Rudy et al. | |
| 4,561,998 A | 12/1985 | Wertz et al. | |
| 4,888,119 A | 12/1989 | Klewsaat | |
| 5,204,010 A | 4/1993 | Klewsaat | |
| 5,441,541 A | 8/1995 | Mehreteah et al. | |
| 5,472,455 A | 12/1995 | Mehreteah et al. | |
| 6,010,996 A | 1/2000 | Hu et al. | |
| 6,210,689 B1 | 4/2001 | Martino et al. | |
| 6,306,805 B1 | 10/2001 | Bratescu et al. | |
| 6,680,286 B1 | 1/2004 | Kawaguchi et al. | |
| 7,026,270 B2 | 4/2006 | Benner et al. | |
| 7,067,499 B2 | 6/2006 | Erazo-Majewicz et al. | |
| 7,097,705 B2 | 8/2006 | Smith et al. | |
| 7,157,409 B2 | 1/2007 | Horton et al. | |
| 7,264,885 B2 | 9/2007 | Rosen et al. | |
| 2009/0281359 A1 | 11/2009 | Daugs et al. | |
| 2011/0015111 A1* | 1/2011 | Yu et al. | 510/351 |
| 2011/0112328 A1* | 5/2011 | Drovetskaya et al. | 564/292 |

FOREIGN PATENT DOCUMENTS

| | | |
|---|---|---|
| WO | 2011/008570 A2 | 1/2011 |
| WO | 2011/056620 A1 | 5/2011 |

OTHER PUBLICATIONS

Fuangswasdi, A. et al., Mixtures of Anionic and Cationic Surfactants with Single and Twin Head Groups: Solubilization and Adsolubilization of Styrene and Ethylcyclohexane. Journal of Surfactants and Detergents (2006), 9 (1), p. 29-37.
Upadhyaya, A., et al, Microemulsion Phase Behavior of Anionic-Cationic Surfactant Mixtures: Effect of Tail Branching. Journal of Surfactants and Detergents (2006), 9(2), p. 169-179.
Kume, G. et al., Review on Anionic-Cationic Surfactant Mixtures. Journal of Surfactants and Detergents (2008), 11 (1), p. 1-11.
Scamehorn, J.F., et al., Precipitation of Surfactant Mixtures. Surfactant Science Series (2005), 124 (Mixed Surfactant Systems (2nd Edition)), p. 601-655.
Amante, J.C., et al. Precipitation of Mixtures of Anionic and Cationic Surfactants. II. Effect of Surfactant Structure, Temperature, and pH. Journal of Colloid and Inteface Science (1991), 144(1), p. 243-253.
Stellner, K. L., et al. Precipitation Phenomena in Mixtures on Anionic and Cationic Surfactants in Aqueous Solutions. Journal of Colloid and Interface Science. (1988). 123(1), p. 186-200.
Doan, T., et al., Formulation Middle-Phase Microemulsions Using Mixed Anionic and Cationic Surfactant Systems. Journal of Surfactants and Detergents (2003), 6(3), p. 215-224.
Joos, P, et al., Dynamic Surface Properties of Anionic-Cationic Mixtures. Journal of Physical Chemistry. (1986), 90 (15), p. 3386-3396.
Wu, Y.F. et al., Synergism in the Spreading of Hydrocarbon-Chain Surfactants on Polyethylene Film-Anionic and Cationic Mixtures by a Two-step Procedure. Langmuir (2005), 21(6), p. 2342-2348.
Shrestha, R.G., et al., Formation of Wormlike Micelle in a Mixed Amino-Acid Based Anionic Surfactant and Cationic Surfactant Systems. Journal of Colloid and Interface Science (2007), 311(1), p. 276-84.

* cited by examiner

*Primary Examiner* — Charles Boyer
(74) *Attorney, Agent, or Firm* — Steven W. Mork

(57) ABSTRACT

Provided are compositions containing a compatible mixture of a cationic surfactant and an anionic surfactant. A composition according to the invention comprises: (a) a first surfactant of formula I:

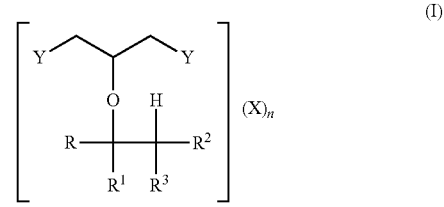

wherein R, $R^1$, $R^2$, and $R^3$ Y, X, and n are as defined below; (b) a second surfactant that is oppositely charged to the first surfactant.

13 Claims, No Drawings

COMPATIBLE MIXTURES OF ANIONIC AND CATIONIC SURFACTANTS

This application claims priority to U.S. provisional application Ser. No. 61/359,403, filed Jun. 29, 2010, which is incorporated herein by reference in its entirety.

FIELD OF THE INVENTION

The invention relates to compositions that comprise compatible mixtures of cationic and anionic surfactants. The compositions are stable in aqueous systems.

BACKGROUND OF THE INVENTION

Mixtures of cationic and anionic surfactants have potential for use in applications in a wide variety of markets, including in household and personal care product formulations. However, it is known that conventional anionic and cationic surfactants are generally not compatible, tending to precipitate when mixed in aqueous solution. Precipitation is undesirable because it renders the surfactants substantially or completely ineffective. Therefore, anionic and cationic surfactants are difficult to mix without the risk of precipitation or instability.

There have been a number of efforts in the prior art to overcome the problem of instability of cationic-anionic surfactant systems. The prior art efforts, however, exhibit various limitations or are overly complex. For instance, prior art efforts require that one component of the oppositely charged pairs be small in molecular size, or one of the components be weakly charged, or that a co-surfactant/bridging surfactant be used.

It would be a significant advance in the art to provide a cationic/anionic surfactant system that is simple, exhibits favorable properties and that is stable in aqueous solution.

BRIEF SUMMARY OF THE INVENTION

The invention provides a composition containing a compatible mixture of anionic and cationic surfactants. More particularly, the composition comprises: (a) a first surfactant of formula I:

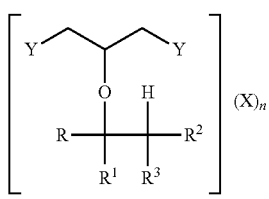

(I)

wherein R, $R^1$, $R^2$, and $R^3$ Y, X, and n are as defined below; (b) a second surfactant that is oppositely charged to the first surfactant.

DETAILED DESCRIPTION OF THE INVENTION

As noted above, the invention provides a composition comprising a first surfactant that is a compound of formula I, and a second surfactant that is oppositely charged to the first surfactant. Advantageously, compositions of the invention are stable and clear in aqueous solution. In addition, as demonstrated by the Examples, in some embodiments compositions of the invention exhibit a synergistic effect with respect to various important surfactant attributes, including foam reduction, static surface tension reduction, and reduction of critical micelle concentration. Further, in some embodiments, the compositions exhibit a remarkable enhancement of wetting/spreading of aqueous solutions on highly hydrophobic surfaces.

The first surfactant of the composition is a compound of the formula I:

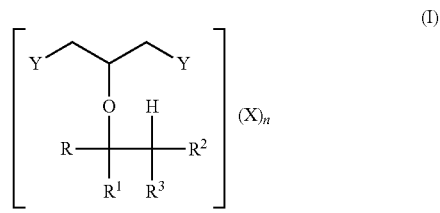

(I)

wherein R is linear or branched $C_2$-$C_{22}$ alkyl; $R^1$, $R^2$, and $R^3$ are independently H or linear or branched $C_1$-$C_{18}$ alkyl; Y is $SO_3^-$ or $N^+R^4R^5R^6$; wherein $R^4$, $R^5$, and $R^6$ are independently $C_1$-$C_4$ alkyl, aryl-$C_1$-$C_4$ alkyl, or $R^4$ and $R^5$, together with the nitrogen to which they are attached, form a ring containing 3-9 carbon atoms; X is a monovalent or divalent ion; n is an integer such that the total ionic charge provided by $X_n$ is 2.

Preferred compounds of formula I include compounds of formula I-1, which are compounds of formula I in which R is linear $C_4$-$C_{16}$ alkyl.

Preferred compounds of formula I and I-1 include compounds of formula I-2, which are compounds of formula I or I-1 in which $R^1$ is H.

Preferred compounds of formula I, I-1, and I-2 include compounds of formula I-3, which are compounds of formula I, I-1, or I-2 in which $R^2$ is H.

Preferred compounds of formula I, I-1, I-2, and I-3 include compounds of formula I-4, which are compounds of formula I, I-1, I-2, or I-3 in which $R^3$ is H.

Preferred compounds of formula I, I-1, I-2, I-3, and I-4 include compounds of formula I-5, which are compounds of formula I, I-1, I-2, I-3, or I-4 in which the total number of carbon atoms in R, $R^1$, $R^2$, $R^3$ and the carbons to which they are attached is 4 to 22, alternatively 5-18, or alternatively 6-14.

Preferred compounds of formula I, I-1, I-2, I-3, I-4, and I-5 include compounds of formula I-6, which are compounds of formula I, I-1, I-2, I-3, I-4, or I-5 in which $R^1$, $R^2$, and $R^3$ are simultaneously H and R is linear $C_2$-$C_{20}$ alkyl, alternatively linear $C_4$-$C_{12}$ alkyl.

Preferred compounds of formula I, I-1, I-2, I-3, I-4, I-5, and I-6 include compounds of formula II, which are compounds of formula I, I-1, I-2, I-3, I-4, I-5, or I-6 in which Y is $SO_3^-$ and X is $H^+$, or a monovalent or divalent cation:

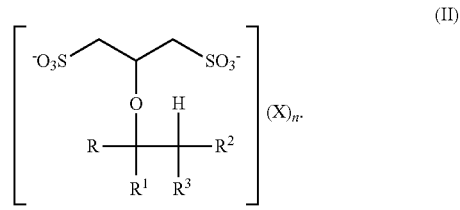

(II)

In some embodiments, X in the compounds of formula II is sodium, potassium, ammonium, calcium, magnesium, or alkylated ammonium. In some embodiments, X is sodium (Na⁺) and n is 2.

In some embodiments, the compound of formula II is sodium 2-hexan-2-yloxypropane-1,3-disulfonate, sodium 2-octan-2-yloxypropane-1,3-disulfonate, sodium 2-decan-2-yloxypropane-1,3-disulfonate, sodium 2-dodecan-2-yloxypropane-1,3-disulfonate, sodium 2-tetradecan-2-yloxypropane-1,3-disulfonate, sodium 2-hexadecan-2-yloxypropane-1,3-disulfonate, or sodium 2-octadecan-2-yloxypropane-1,3-disulfonate.

Preferred compounds of formula I, I-1, I-2, I-3, I-4, I-5, and I-6 also include compounds of formula III, which are compounds of formula I, I-1, I-2, I-3, I-4, I-5, or I-6 in which Y is $N^+R^4R^5R^6$ and X is a monovalent or divalent anion:

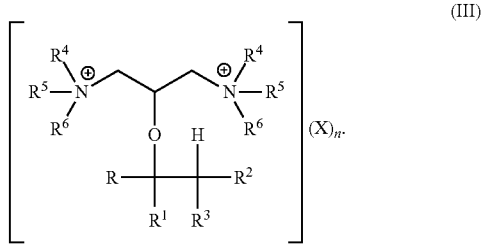

In some embodiments, X in the compounds of formula III is halide (chloride, bromide, or iodide), bicarbonate, carbonate, sulfate, methyl sulfate or bisulfate. In some embodiments, X is chloride (Cl⁻) and n is 2.

In some embodiments, $R^4$, $R^5$, and $R^6$ are each methyl.

In some embodiments, the compound of formula III is: N,N,N',N',N'-hexamethyl-2-(1-methylheptanyloxy)-1,3-propanediaminium dichloride; N,N,N,N',N',N'-hexamethyl-2-(1-methylnonanyloxy)-1,3-propanediaminium dichloride; N,N,N,N',N',N'-hexamethyl-2-(1-methylundecyloxy)-1,3-propanediaminium dichloride; N,N,N,N',N',N'-hexamethyl-2-(1-methyltridecyloxy)-1,3-propanediaminium dichloride; N,N,N,N',N',N'-hexamethyl-2-(1-methylpentadecyloxy)-1,3-propanediaminium dichloride; N,N,N,N',N',N'-hexamethyl-2-(1-methyltridecyloxy)-1,3-propanediaminium dichloride; N,N,N,N',N',N'-hexamethyl-2-(1-methylheptadecyloxy)-1,3-propanediaminium dichloride; N,N,N,N',N', N'-hexaethyl-2-(1-methylpentadecyloxy)-1,3-propanediaminium dichloride; N,N,N',N'-tetraethyl-N,N'-dimethyl-2-(1-methylpenta-decyloxy)-1,3-propanediaminium dichloride; N,N,N',N'-tetraethyl-N,N'-dibenzyl-2-(1-methylpentadecyloxy)-1,3-propanediaminium dichloride; N,N,N,N',N',N'-hexamethyl-2-(1-ethyldecyloxy)-1,3-propanediaminium dichloride; and N,N,N,N',N',N'-hexamethyl-2-(1-ethyltetradecyloxy)-1,3-propanediaminium dichloride.

The processes described below for preparing the compounds of formula I may result in the formation of mixtures of formula I compounds. Although the individual formula I compounds may be isolated from the mixture, this step is not necessary, and indeed it is sometimes preferred that the compounds be used in the form of the mixture. Thus, mixtures of formula I compounds are contemplated and are within the scope of the invention.

In addition, the processes may result in the formation of the mono-functional derivatives of the formula I compounds. For instance, in preparing compounds in which Y is $SO_3^-$ (i.e., compounds of the formula II), the processes may also result in the formation of compounds of formula IIA:

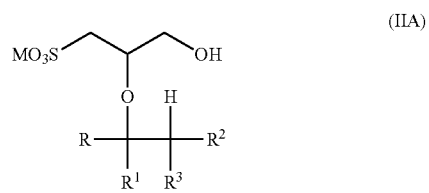

wherein M is H⁺ or a monovalent or divalent cation, and R, $R^1$, $R^2$, and $R^3$ are as defined above for compounds of formula I. Accordingly, in some embodiments, the compositions of the invention may further comprise the mono-functional derivatives of the formula I compounds, such as compounds of formula IIA.

The second surfactant of the composition of the invention is a compound that is oppositely charged to the first surfactant. Thus if the first surfactant has an overall anionic charge, then the second surfactant has an overall cationic charge. Conversely, if the first surfactant has an overall anionic charge, then the second surfactant has an overall cationic charge.

There is no particular limitation on the surfactant that may be used as the second surfactant, provided only that the compound carry an overall charge that is opposite to the first surfactant, as described above. Examples of compounds that are suitable for use as the second surfactant include, but are not limited to, hexyltrimethylammonium bromide or chloride, octyltrimethylammonium bromide or chloride, decyltrimethylammonium bromide or chloride, n-dodecyl trimethylammonium bromide or chloride, n-dodecyl ethyldimethylammonium bromide or chloride, tetradecyltrimethylammonium bromide or chloride, tetradecyl ethyldimethylammonium bromide or chloride, n-hexadecyl trimethylammonium bromide or chloride, C4-C16 alkylpyridinium chloride or bromide, dodecyldimethylbenzonium chloride, an alcohol sulfate such as sodium dodecyl sulfate, sodium linear alkylbenzene sulfonate, an alcohol ether sulfate, an alkanesulfonate, an alkyldiphenyloxide disulfonate salt such as hexyldiphenyloxide disulfonate salt or hexadecyldiphenyloxide disulfonate salt, or combinations of two or more thereof.

In a particular embodiment, the second surfactant is a compound of IV, which is a compound of formula I that carries an overall opposite charge to that of the first surfactant compound:

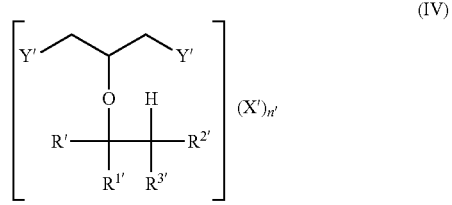

wherein R', $R^{1'}$, $R^{2'}$, and $R^{3'}$ Y', X', and n' carry the same definitions as indicated above for groups R, $R^1$, $R^2$, and $R^3$ Y, X, and n, respectively, including preferred embodiments thereof as described. It should be noted that in the compositions of the invention, the groups R, $R^1$, $R^2$, and $R^3$ Y, X, and n of formula I and the groups R', $R^{1'}$, $R^{2'}$, and $R^{3'}$ Y', X', and n' of formula IV are independently selected. That is, in compositions of the invention that comprise a compound of formula IV as the second surfactant, R', $R^{1'}$, $R^{2'}$, and $R^{3'}$ Y', X', and n' may or may not be the same as the groups R, R$^1$, R$^2$, and R$^3$ Y, X, and n of the first surfactant.

In another particular embodiment of the invention, the first surfactant of the composition is a cationic surfactant of formula III and the second surfactant is an anionic surfactant of formula V:

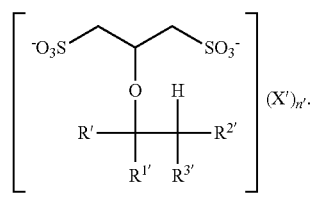
(V)

In still further particular embodiments, the first surfactant is cationic and is N,N,N,N',N',N'-hexamethyl-2-(1-methylheptanyloxy)-1,3-propanediaminium dichloride;

N,N,N,N',N',N'-hexamethyl-2-(1-methylnonanyloxy)-1,3-propanediaminium dichloride;

N,N,N,N',N',N'-hexamethyl-2-(1-methylundecyloxy)-1,3-propanediaminium dichloride;

N,N,N,N',N',N'-hexamethyl-2-(1-methyltridecyloxy)-1,3-propanediaminium dichloride;

N,N,N,N',N',N'-hexamethyl-2-(1-methylpentadecyloxy)-1,3-propanediaminium dichloride;

N,N,N,N',N',N'-hexamethyl-2-(1-methyltridecyloxy)-1,3-propanediaminium dichloride;

N,N,N,N',N',N'-hexamethyl-2-(1-methylheptadecyloxy)-1,3-propanediaminium dichloride;

N,N,N,N',N',N'-hexaethyl-2-(1-methylpentadecyloxy)-1,3-propanediaminium dichloride;

N,N,N',N'-tetraethyl-N,N'-dimethyl-2-(1-methylpenta-decyloxy)-1,3-propanediaminium dichloride; N,N,N',N'-tetraethyl-N,N'-dibenzyl-2-(1-methylpentadecyloxy)-1,3-propanediaminium dichloride; N,N,N,N',N',N'-hexamethyl-2-(1-ethyldecyloxy)-1,3-propanediaminium dichloride; N,N,N,N',N',N'-hexamethyl-2-(1-ethyltetradecyloxy)-1,3-propanediaminium dichloride; or mixtures of two or more thereof, and the second surfactant is anionic and is: sodium 2-hexan-2-yloxypropane-1,3-disulfonate; sodium 2-octan-2-yloxypropane-1,3-disulfonate; sodium 2-decan-2-yloxypropane-1,3-disulfonate; sodium 2-dodecan-2-yloxypropane-1,3-disulfonate; sodium 2-tetradecan-2-yloxypropane-1,3-disulfonate; sodium 2-hexadecan-2-yloxypropane-1,3-disulfonate; sodium 2-octadecan-2-yloxypropane-1,3-disulfonate; or mixtures of two or more thereof.

Compounds of formula I may be prepared as described in U.S. patent application Ser. No. 12/430,171, filed Apr. 27, 2009, U.S. patent application No. 61/226,109, filed Jul. 16, 2009, and U.S. patent application No. 61/258,803, filed Nov. 6, 2009, each of which is incorporated herein by reference in its entirety.

By way of example of the synthetic procedure, a dihalogenated (preferably dichloride) ether compound of formula A is first synthesized by the reaction of an alcohol compound with an olefin in the presence of an acidic etherification catalyst:

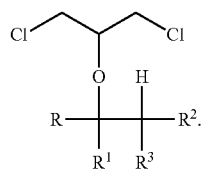
(A)

Typically, an equimolar or slight excess of the olefin is used. A solvent may be used, although not required. The reaction may be conducted at elevated temperature, such as about 50 to 150° C. Once the desired amount of the ether compound product is formed (as determined, for instance, by gas chromatography), the reaction mixture is cooled and subjected to conventional workup. For instance, for removal of a homogeneous acid catalyst, the cooled mixture is added to water containing bicarbonate and/or chloride salts, and the organic liquid layer of the mixture containing the ether compound removed. The ether compound may be further purified by known techniques, such as distillation.

Preferred alcohols for the synthesis include: 1,3-dihalo-2-propanol and 2,3-dihalopropanol, or a mixture thereof. Particularly preferred are 1,3-dichloro-2-propanol and 2,3-dichloropropanol, or a mixture thereof.

The olefin for use in the above synthesis is preferably a linear or branched alpha-olefin (i.e., 1-alkenes) containing 4 to 22 carbon atoms, or a mixture of isomers of linear or branched 1-alkenes containing 4 to 22 carbon atoms together with their internal and/or tertiary olefin isomers. Preferably, the alkenes are linear and contain 6 to 18 carbon atoms. Non-limiting examples of particularly preferred alpha olefins include: 1-butene, 1-pentene, 1-hexene, 4-methyl-1-pentene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, or mixtures of two or more thereof.

As the olefin may be isomerized when contacted with the acidic etherification catalyst, it is not necessary to use an alpha-olefin, and internal olefins containing 4 to 22 carbon atoms, or mixtures of isomers of linear or branched alkenes are also suitable for use. Non-limiting examples of suitable internal olefins include: 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene, etc, or mixtures of two or more thereof.

Acidic etherification catalysts suitable for use in the synthesis of the ether compound include, but are not limited to, acidic ionic exchange resins, such as DOWEX DR-2030 available from The Dow Chemical Company, clays, zeolites, sulfonated polystyrene beads, and acids immobilized on a heterogeneous surface, such as tetrafluoroethanesulfonic acid on silica beads, Bronsted acids such as triflic (trifluoromethanesulfonic) acid, methanesulfonic acid, or sulfuric acid, Lewis acids such as BF3 and its derivatives (e.g., dihydrate or ether), and trimethylsilyl triflate. The ratio of catalyst to reactants is not critical and is generally adjusted so as to obtain a desired reaction rate. Preferably, the catalyst is at a temperature of between about 50 and 150° C. during the process in order to facilitate the etherification reaction.

The dihalogenated ether compound of formula I may be used to prepare formula I compounds in which Y is SO$_3^-$ or formula I compounds in which Y is N$^+$R$^4$R$^5$R$^6$ (analogously for formula IV compounds). For instance, for compounds in which Y is SO$_3^-$, the formula A compound is typically subjected to a sulfonation reaction in which the compound is contacted with a sulfonating agent, such as sodium sulfite or combination of sodium sulfite and sodium carbonate. The reaction may be conducted in water and may be carried out at elevated temperature and pressure, such as 150 to 220° C. and 100 to 350 psig. Following sufficient time for the reaction to occur (e.g., 24 hours), the reaction mixture is cooled and de-pressurized to ambient conditions, and then subjected to conventional workup. The sulfonated compound may optionally be further purified. Purification may be conducted using conventional techniques, such as extraction, filtration, chromatography, and/or crystallization. If desired, excess sulfite may be oxidized to sulfate by, for example, addition of hydrogen peroxide.

Other typical methods for introducing the sulfonate functionality, such as reaction of the ether compound with a sulfide or polysulfide, then oxidation, may also be used to generate the compounds of formula I.

The disulfonate formula I compounds may be prepared from the dihalogenated ether starting material (formula A) as described above. If both halogens are displaced by the sulfonating agent, then the disulfonate compound is formed. If both displacement and hydrolysis takes place, then the hydroxy sulfonate of formula II-A (shown above) is also formed.

As example of the synthesis of compounds in which Y is $N^+R^4R^5R^6$, the formula A compound is typically first reacted to form a diamine ether precursor of the desired compound, followed by reaction with an alkylating agent under ionizing conditions. Thus, the formula A compound may be reacted with a large excess of a dialkylamine at elevated pressure and temperature, such as in a sealed reactor at 100 to 120° C., and for sufficient time for the reaction to occur, e.g., 24 hours. The reaction may be conducted under inert atmosphere, and a solvent may be used, e.g., water. Following reaction, the mixture is allowed to cool and the pressure discharged. Typical workup may be used to isolate the diamine ether compound.

The formula I compound in which Y is $N^+R^4R^5R^6$, is typically prepared by reacting the diamine ether compound described above with a haloalkyl compound, under ionizing conditions. "Ionizing conditions" include a temperature of 20 to 250, preferably 35 to 200 and more preferably 50 to 150° C. Ionizing conditions may also include a solvent to facilitate the reaction, e.g., water, alcohols, ethers, nitriles, N,N-dialkylamides and the like, or mixtures thereof. The upper limit on the temperature is such as to avoid Hoffman degradation of the reaction product. Pressure is a function of the solvent and alkylating agent. The optional solvent should be sufficiently polar to allow the intermediate mono-quaternary amine compound to remain in solution at the reaction temperature. Residence time is a function of the substrates and temperature. Typically, the reaction time is sufficient to completely convert the diamine to di-quat, and this time is generally greater than one hour and can be as long as 24 hours or more. The process is usually performed without a catalyst. The final desired product may be isolated by typical work-up techniques well known to those skilled in the art.

Compositions of the invention may be used in a wide variety of applications where the presence of surfactants is desired or needed. By way of non-limiting example, the compositions may be used as or in: agrochemicals formulations, cleaning formulations, emulsion polymerization, paints & coatings, formulations for use in pulp and paper processing, textile processing, personal care applications, oilfield applications, and water treatment.

The amount of the composition to be used in surfactant applications varies depending on the application and the desired result The amount may be determined by a person of ordinary skill in the art without undue experimentation. Generally, a formulation that includes therein a composition of the invention will contain at least about 0.01 weight percent of the composition, based on the total weight of the formulation.

There is no particular limitation on the weight ratios of the first surfactant to the second surfactant in the invention compositions, and indeed it is one of the advantages of the invention that stable aqueous compositions may be obtained at a wide ratio range, In some embodiments, the weight ratio of the first surfactant to the second surfactant is in the range of 1:99 to 99:1, alternatively 20:80 to 80:20, alternatively 40:60 to 60:40, or alternatively 50:50. As noted above and demonstrated by the Examples, at some ratios, particularly those in the range of 40:60 to 60:40, and more particularly at about 50:50, compositions of the invention advantageously exhibit synergy with respect to various important surfactant properties, including foam reduction, static surface tension reduction, and reduction of critical micelle concentration.

The following examples are illustrative of the invention but are not intended to limit its scope. Unless otherwise indicated, the ratios, percentages, parts, and the like used herein are by weight.

EXAMPLES

Example 1A

Preparation of N,N,N,N',N',N'-hexamethyl-2-(1-methylundecyloxy)-1,3-propanediaminium dichloride ("C12 Di-Quat")

Step 1: Preparation of $C_{12}$-diamine2 (N,N,N',N'-tetramethyl-2-(1-methylundecyloxy)-1,3-propanediamine from 1,3-dichloropropan-2-yloxydodecanes A $N_2$-purged 450-mL Parr reactor equipped with a propeller-type impeller and removable glass liner is charged with 17.7 grams (g) of $N_2$-sparged 1,3-dichloropropan-2-yloxydodecanes (59.5 mmol) via syringe. The reactor is then loaded via cannula with 115.8 g dimethylamine solution (40% in water, Aldrich; 1.028 mmol; 17.3 eq.) which is not de-aerated. The reactor is sealed, and agitation and heating initiated. The temperature reaches a maximum of 119° C. within 100 min and then is stabilized between 106-108° C. for 16 hours. The reactor is then allowed to cool to 80° C. and the pressure is slowly released via a gas disperser into a large amount of 1 N HCl. The reactor is opened at room temperature, revealing a cloudy-white lower layer and a very thin, dark upper layer. These are separated by addition of 100 mL diethyl ether and the aqueous layer is washed twice with 75 mL ether. The combined organic fractions are dried over anhydrous $MgSO_4$, filtered, and reduced by rotary evaporation to an oil. This is then distilled at 0.6-0.9 mmHg and 129-136° C. using a short-path micro-distillation apparatus. Yield of clear, colorless, slightly viscous oil: 14.44 g (FW=314.55, 77%). $^1$H NMR ($CHCl_3$), ppm: (δ) 3.3-3.75 (m, 2.3H); 2.2-2.4 (m, with two strong non-equal peaks, 13H); 1.5 (br m), 1.24 (br s), 1.12 (d, 6 Hz), 0.87 (m); total alkyl integral (0.8-1.6) 24H. $^{13}$C NMR ($CHCl_3$), ppm: (δ) 79.2, 63.3, 63.1, 46.7, 37.4, 32.1, 30.0, 29.5, 25.9, 22.8, 20.6, 14.3 (minor peaks also seen at 44.2, 43.9, 43.8, 26.9, 25.6). Calcd. for $C_{19}H_{42}N_2O$ (%): C, 72.55; H, 13.46; N, 8.91; O, 5.09; Cl, 0. Found: C, 71.36; H, 13.14; N, 7.92; O, 4.58; Cl, 0.38.

Step 2: Preparation of C12-Diquat from $C_{12}$ Diamine2

A $N_2$-purged 450-mL Parr reactor equipped with a propeller-type impeller and removable glass liner is charged with a mixture of 40 mL methanol and 10 mL water and stirring initiated. The reactor is then sealed and placed under nitrogen by 10 pressurizations to 32 psi followed by venting to atmospheric pressure. After three pressurizations to 30 psi with chloromethane followed by venting to atmospheric pressure, the reactor is allowed to fill with chloromethane to a pressure of 50 psi at 30° C. at which point the flow of chloromethane is stopped. After 5 minutes the reactor temperature falls to 25° C. and the pressure to 40-45 psi. Through a septum port are added 8.01 g $C_{12}$-diamine2 (25.5 mmol). The reactor is then heated to 89-95° C. for 17.5 hours during which time the pressure rises to 90 psi before falling to 75-80 psi. After cooling and venting the reactor, the reaction mixture, a brownish oily liquid, is reduced to a thick tar by rotary evaporation. Ethanol (50 mL) is added and removed by rotary evaporation twice. Then ethanol (80 mL) is added and the resulting solid filtered, washed with ethanol, and dried to a pale blue powder (2.42 g). The filtrate is concentrated to a dark oil, mixed with 80 mL diethyl ether, and agitated overnight. The resulting wet cake is centrifuged, and the supernatant discarded. More diethyl ether is added, and the blue solid filtered and washed with more diethyl ether. After drying in air, the solid turns to a tarry green wax. The sample contains 16.6 wt % inorganic chloride by $AgNO_3$ titration (theoretical 17.1) and 5% water by Karl Fischer titration. Yield 7.67 g (FW=415.52, 69%, corrected for water). Proton NMR spectrum consists of broad, overlapping peaks. $^1H$ NMR ($CD_3OD$), ppm: ($\delta$) 3.69 (br m), 3.30 (br s), 2.98 (br s), 1.69 (br m), 1.26 (br s), 1.15 (m), 0.94 (br s), 0.86 (br s). The ratio of total integrals for the region 4.1-2.6 ppm to that for the region 2.0-0.6 ppm=22.4:24 (theor. 24:24). NMR spectra are collected on a Varian Inova 400 MHz spectrometer. Elemental analyses are provided by Quantitative Technologies, Inc., Whitehouse, N.J.

Example 1B

Preparation of N,N,N,N',N',N'-hexamethyl-2-(1-methylpentadecyloxy)-1,3-propanediaminium dichloride ("C16 Di-Quat")

Step 1: Preparation of N,N,N',N'-tetramethyl-2-(1-methylpentadecyloxy)-1,3-propanediamine ($C_{16}$-diamine2) from 1,3-dichloropropan-2-yloxyhexadecanes A $N_2$-purged 450-mL Parr reactor equipped with a propeller-type impeller and removable glass liner is charged with 26.80 g of 1,3-dichloropropan-2-yloxyhexadecanes (75.8 mmol) via syringe and 130.35 g dimethylamine solution (40% in water, Aldrich; 1.157 mmol; 15.3 eq.) via cannula. The reactor is sealed under 10 psi $N_2$, and heated to 105-116° C. (90-110 psi) for 19 hours. After cooling to 30° C., the reactor is allowed to vent and is then purged with flowing $N_2$ for about 75 min. The reactor contents are poured into a separatory funnel with 200 mL water and 100 mL hexanes. The aqueous fraction is washed twice with 100 mL hexanes and the combined organic fractions are dried over anhydrous $MgSO_4$ and reduced by rotary evaporation to a clear yellow oil. The product is distilled using a short-path jacketed column at 0.27-0.34 mmHg and 159-168° C. Yield of clear, colorless, slightly viscous oil: 24.822 g (FW=370.39, 88%). $^1H$ NMR ($CHCl_3$), ppm: ($\delta$) 3.3-3.8 (m, 2.9H); 2.2-2.5 (m, with two strong non-equal peaks, 13H); 1.5 (br m), 1.26 (br s), 1.14 (d, 6 Hz), 0.89 (m); total alkyl integral (0.8-1.6) 32H.

Step 2: Preparation of C16 Di-Quat from C16-diamine2

A 450-mL Parr reactor with an impeller removed and thermocouple housing sheathed by a glass NMR tube section containing mineral oil and sealed with PTFE tape and with removable glass liner containing a magnetic stirbar is sealed and purged with $N_2$. To the reactor is added 5 mL water and a $N_2$-sparged mixture of 15.42 g $C_{16}$-diamine2 (41.6 mmol) and 55.70 g methanol. The reactor is rapidly pressurized with chloromethane (Aldrich, 99.5%) and depressurized for three cycles, then allowed to equilibrate with the tank of chloromethane for 16 minutes after which the tank is closed and the reactor heated to 86-7° C. for 19 hours. After cooling to 36° C. the reactor is vented and then purged with $N_2$ flow for 6 minutes. The resulting clear, green solution is reduced to an amber oil by rotary evaporation. To the soapy cake is then added 50 mL ethanol, which is removed by rotary evaporation, followed by a second ethanol charge of 100 mL, which is also similarly removed. A mixture of the resulting solid in ethyl ether and hexanes could not be filtered, so it is allowed to dry in air and then by vacuum drying (42° C., overnight). Yield of waxy solid: 18.41 g. Proton NMR spectrum consisted of broad, overlapping peaks. $^1H$ NMR ($CD_3OD$), ppm: ($\delta$) 3.5-3.8 (br m), 3.3 (br s), 3.0 (br s), 1.26 (br s), 1.15 (m), 0.94 (br s), 0.87 (m). The ratio of total integrals for the region 4.1-2.9 ppm to that for the region 2.0-0.6 ppm=19.6:32 (theor. 24:32). $^{13}C$ NMR ($CD_3OD$), ppm: ($\delta$) 74.4, 70.0, 69.6, 69.2, 66.8, 38.0, 33.1, 30.5-31.1, 26.4-26.8, 23.7, 20.8, 19.9, 18.8, 14.5 (with many minor peaks). Calcd. for $C_{25}H_{56}Cl_2N_2O$ (%): C, 63.67; H, 11.97; N, 5.94; Cl, 15.03. Found: C, 60.68; H, 11.73; N, 4.41; Cl, 15.29. Inorganic chloride ($AgNO_3$ titration): 12.6 wt % (theoretical 15.0) and 3.3% water by Karl Fischer titration. Transition metal contents (ICP): Fe, 0.31%; Cr, 0.17%; Ni, 0.04%.

C8 Diquat, C10 Diquat, and C14 Diquat may be prepared substantially as described above in Examples 1A and 1B using appropriate substitutions of starting materials.

Example 2A

General Preparation of Sulfonates with Sodium Sulfite/Meta-Bisulfite

A 2 L Parr reactor is charged with 0.456 mol of the alkyl 1,3-dichloropropyl ether, 0.783 mol of sodium sulfite, 0.180 mol of sodium meta-bisulfite, 0.289 mol of sodium carbonate, and 590 g of water. Following a nitrogen flush and pressure check, the system is heated to 200° C. for 20 hours. The pressure after reaching temperature is 250 psig. The solution is cooled to ambient temperature and unloaded to afford the reaction product.

Example 2B

Preparation of Sodium 2-Decan-2-yloxypropane-1,3-disulfonate ("C10 Disulfonate")

The compounds are made substantially as described in Example 2A above, using appropriate substitutions of starting materials (138.6 g of 1,3-dichloro-2-propan-2-yloxydecane, 112.5 g of sodium sulfite, 39.0 g of sodium meta-bisulfite, 34.52 g of sodium carbonate, 550.43 g of water, 190° C., 20 hours). Following reaction, the reaction mixture is cooled to ambient temperature and unloaded to afford 826.5 g of light brown reaction product.

Example 2C

Preparation of Sodium 2-Dodecan-2-yloxypropane-1,3-disulfonate ("C12 Disulfonate")

The compounds are made substantially as described in Example 2A above, using appropriate substitutions of starting materials (135.5 g of 1,3-dichloro-2-propan-2-yloxy-dodecane, 98.66 g of sodium sulfite, 34.18 g of sodium meta-bisulfite, 30.66 g of sodium carbonate, 590 g of water, 200° C., 20 hours). Following reaction, the reaction mixture is cooled to ambient temperature and unloaded to afford 865.3 g of light brown reaction product.

Example 2D

Preparation of Sodium 2-Hexadecan-2-yloxypropane-1,3-disulfonate ("C16 Sulfonate"

The compounds were made substantially as described in Example 2A above, using appropriate substitutions of starting materials (87.10 g of 1,3-dichloro-2-propan-2-yloxy-hexadecane, 53.57 g of sodium sulfite, 19.83 g of sodium meta-bisulfite, 19.11 g of sodium carbonate, 558.44 g of water, 207° C., 31 hours). Following reaction, the reaction mixture is cooled to ambient temperature and unloaded to afford 677 g of product.

Example 3

Evaluation of Invention Compositions

In the following Examples, aqueous solutions are made with de-ionized water. Static surface tension is measured using a Krüss Tensiometer K-100 with Wilhelmy plate at 25° C. Dynamic surface tension is measured using a Krüss Bubble Pressure Tensiometer BP-2 at 25° C. The foam profile is compared by placing 10 grams of solution in a 40 mL vial and shaking it vigorously for 30 sec, then standing it by to note foam profile at room temperature. Wetting is determined by measuring contact angle on Teflon surface using a Kruss DSA-100 at 25° C.

Compatibility of anionic and cationic surfactants is justified by stability of aqueous solution of the anionic-cationic surfactant mixtures. Stability is based on clarity of the solutions after 2 weeks. Crystal clear indicates excellent stability; clear indicates good stability; cloudy indicates poor stability; and a white precipitate indicates very poor stability.

Abbreviations used are as follows:

C8 Diquat: N,N,N,N',N',N'-hexamethyl-2-(1-methylheptanyloxy)-1,3-propanediaminium dichloride:

C10 Diquat: N,N,N,N',N',N'-hexamethyl-2-(1-methylnonanyloxy)-1,3-propanediaminium dichloride.

C12 Diquat: N,N,N,N',N',N'-hexamethyl-2-(1-methylundecyloxy)-1,3-propanediaminium dichloride.

C14 Diquat: N,N,N,N',N',N'-hexamethyl-2-(1-methyltridecyloxy)-1,3-propanediaminium dichloride.

C16 Diquat: N,N,N,N',N',N'-hexamethyl-2-(1-methylpentadecyloxy)-1,3-propanediaminium dichloride.

C10 Disulfonate: sodium 2-decan-2-yloxypropane-1,3-disulfonate:

C12 Disulfonate: sodium 2-dodecan-2-yloxypropane-1,3-disulfonate.

C16 Disulfonate: sodium 2-hexadecan-2-yloxypropane-1,3-disulfonate.

C12 TAB: n-dodecyl trimethylammonium bromide.

C16 TAB: n-hexadecyl trimethylammonium bromide.

DPO-C6: an hexyldiphenyloxide disulfonate anionic surfactant from The Dow Chemical Company.

DPO-C16: an hexadecyldiphenyloxide disulfonate anionic surfactant from The Dow Chemical Company.

DOWFAX™ 2A1: an alkyldiphenyloxide disulfonate anionic surfactant from The Dow Chemical Company.

LAS: sodium linear alkylbenzene sulfonate anionic surfactant.

NaOleate: Sodium oleate.

DTAC (or C12 TAC): dodecyltrimethylammonium chloride.

CTAC (or C16 TAC): cetyltrimethylammonium chloride.

Example 3A

Disulfonate and Diquat Compositions

This Example demonstrates stability and synergism in surface tension reduction of disulfonate/diquat surfactant mixtures of the invention. Data are shown in Table 1. Total surfactant concentrations in the Table are 1000 ppm.

TABLE 1

| Surfactant or Mixture | Wt. ratio | Stability | Static Surface Tension γ (mN/m) | Dynamic Surface Tension | | |
|---|---|---|---|---|---|---|
| | | | | 0.1 b/s | 4 b/s | 10 b/s |
| C12 Disulfonate | 100 | Excellent | 35.5 | 53.5 | 57.6 | 60.9 |
| C12 Disulfonate/C16 Di-Quat | 80/20 | Excellent | 28.6 | 47.8 | 68.6 | 69.6 |
| C12 Disulfonate/C16 Di-Quat | 60/40 | Excellent | 29.1 | 35.5 | 64.8 | 69.2 |
| C12 Disulfonate/C16 Di-Quat | 50/50 | Excellent | 29.4 | 32.5 | 58.4 | 64.4 |
| C12 Disulfonate/C16 Di-Quat | 40/60 | Excellent | 30.2 | 34.8 | 65.5 | 70.7 |
| C12 Disulfonate/C16 Di-Quat | 20/80 | Good | 31.5 | 43.6 | 66.0 | 68.1 |
| C16 Di-quat | 100 | Excellent | 40.6 | 59.2 | 62.0 | 63.7 |
| C16 Disulfonate | 100 | Excellent | 36.0 | 43.6 | 60.0 | 65.8 |
| C16 Disulfonate/C16 Di-Quat | 80/20 | Good | 38.1 | 50.5 | 66.2 | 69.4 |
| C16 Disulfonate/C16 Di-Quat | 60/40 | Excellent | 28.3 | 61.9 | 71.1 | 72.8 |
| C16 Disulfonate/C16 Di-Quat | 50/50 | Excellent | 28.6 | 67.6 | 68.6 | 68.7 |
| C16 Disulfonate/C16 Di-Quat | 40/60 | Excellent | 28.7 | 59.7 | 69.8 | 71.1 |
| C16 Disulfonate/C16 Di-Quat | 20/80 | Good | 29.4 | 61.0 | 68.2 | 70.2 |
| C16 Di-quat | 100 | Excellent | 40.6 | 59.2 | 62.0 | 63.7 |

Example 3B

Disulfonate and Cationic Surfactant Compositions

This Example demonstrates stability and synergism in surface tension reduction of additional disulfonate/cationic surfactant mixtures of the invention. Data are shown in Table 2. Total surfactant concentrations in the Table are 1000 ppm.

TABLE 2

| Surfactant or Mixture | Wt. ratio | Stability | Static Surface Tension γ (mN/m) | Dynamic Surface Tension | | |
|---|---|---|---|---|---|---|
| | | | | 0.1 b/s | 4 b/s | 10 b/s |
| C12 Disulfonate/C12 TAB | 50/50 | Excellent | 26.6 | 24.7 | 35.5 | 45.7 |
| C12 Disulfonate/C16 TAB | 50/50 | Good | 27.2 | 35.8 | 70.7 | 71.0 |
| C16 Disulfonate/C12 TAB | 50/50 | Good | 27.6 | 34.3 | 67.2 | 70.3 |
| C16 Disulfonate/C16 TAB | 50/50 | Excellent | 26.7 | 39.7 | 71.5 | 71.8 |
| C12 TAB | 100 | Excellent | 59.0 | 61.8 | 63.2 | 64.5 |
| C16 TAB | 100 | Excellent | 37.7 | 38.5 | 44.6 | 50.5 |

Example 3C

Diquat and Anionic Surfactant Compositions

This Example demonstrates compatibility of diquat/anionic surfactant mixtures of the invention. Data are shown in Table 3. Total surfactant concentrations in the Table are 1000 ppm.

TABLE 3

| Surfactant or Mixture | Wt. ratio | Stability |
|---|---|---|
| DPO-C6/C16 Di-quat | 50/50 | Excellent |
| DPO-C16/C16 Di-quat | 50/50 | Good |

TABLE 3-continued

| Surfactant or Mixture | Wt. ratio | Stability |
|---|---|---|
| Na Oleate/C16 Di-quat | 50/50 | Good |
| C16 Di-quat | 100 | Excellent |

Example 3D

This Example demonstrates compatibility of C10 Disulfonate and C12 Disulfonate with C8 Diquat, C10 Diquat, C12 Diquat, C14 Diquat, and C16 Diquat, and with cationic surfactants C12 TAC and C16 TAC. Data are shown in Table 4. Total surfactant concentrations in the Table are 10000 ppm.

TABLE 4

| | C10 Disulfonate | C12 Disulfonate |
|---|---|---|
| C8 Diquat | Excellent | Excellent |
| C10 Diquat | Excellent | Excellent |
| C12 Diquat | Excellent | Excellent |
| C14 Diquat | Excellent | Excellent |
| C16 Diquat | Excellent | Excellent |

TABLE 4-continued

|  | C10 Disulfonate | C12 Disulfonate |
| --- | --- | --- |
| C12 TAC | Excellent | Poor |
| C16 TAC | Excellent | Poor |

Example 3E

This Example demonstrates compatibility of C10 Disulfonate surfactant with cationic surfactants C12 TAC, C16 TAC, and C12 Diquat. Data are shown in Table 5. Total surfactant concentrations in the Table are 20000 ppm.

TABLE 5

|  | C10 Disulfonate |
| --- | --- |
| C12 Di-quat | Excellent |
| C12 TAC | Excellent |
| C16 TAC | Excellent |

Example 3F

This Example demonstrates Critical Micelle Concentration (CMC) Reduction of C10 Disulfonate surfactant with cationic surfactant C12 TAC. Data are shown in Table 6. Total surfactant concentrations in the Table are 0.04M.

TABLE 6

| Surfactant or Mixture | Wt. ratio | CMC, ppm |
| --- | --- | --- |
| C12 Disulfonate | 100 | 253 |
| C12 Disulfonate/C12 TAC | 80:20 | 63 |
| C12 Disulfonate/C12 TAC | 60:40 | 165 |
| C12 Disulfonate/C12 TAC | 30:70 | 323 |
| C12 TAC | 100 | 889 |

Example 3G

Into a 40 ml sample, 10 ml of a surfactant solution or a mixture of surfactant solutions at the total concentration of 1000 ppm is added. The sample vial containing the sample is capped and then vigorously shaken by hand at room temperature for 30 seconds. The foam volume in the sample vial is measured after 1 minute and recorded in Table 7 below. The results demonstrate that mixtures of cationic and anionic surfactants according to the invention results in significantly lower foaming than for the surfactants when used alone.

TABLE 7

| Sample | Wt. ratio | Foam Vol. (ml) |
| --- | --- | --- |
| C12 Disulfonate | 100 | 20 |
| C12 Disulfonate/C16 di-quat | 50:50 | 5 |
| C16 Disulfonate | 100 | >30 |
| C16 Disulfonate/C16 di-quat | 50:50 | 5 |
| C16 di-quat | 100 | 22 |

Example 3H

This Example demonstrates Contact Angle Reduction with C10 Disulfonate surfactant cationic surfactant, C12 TAC, and mixtures. Total surfactant concentrations in the Table are 0.04M. Contact angle is measured using Kruss DSA-100 Drop Shape Analyzer in the "sessile" mode. Teflon tape (plumber's tape) is carefully placed on glass microscope slide, using a small amount of adhesive on the each edge of the microscope slide to hold the Teflon tape on the surface. 5 drops of a liquid are placed in different locations on the Teflon tape, drop volumes being 5 µl. The contact angle measurements are recorded in the Table 8 below. The results demonstrate that mixtures of cationic and anionic surfactants according to the invention result in increased wetting on teflon than when the surfactants are used alone.

TABLE 8

| Sample | Wt. ratio | Contact Angle, deg |
| --- | --- | --- |
| C10 Disulfonate | 100 | 97 |
| C10 Disulfonate/C12 TAC | 30:70 | 64 |
| C10 Disulfonate/C12 TAC | 60:40 | 61 |
| C10 Disulfonate/C12 TAC | 80:20 | 56 |
| C12 TAC | 100 | 86 |

Example 4

This Example demonstrates improvement in cleaning efficiency of C12 and C14 Disulfonate surfactants with cationic surfactant BARQUAT (dodecyldimethylbenzonium chloride). Soil is comprised of 33 wt % vegetable shortening, 33 wt % lard, 33 wt % vegetable oil, and 1 wt % carbon black. White vinyl flooring tiles are used as substrates. The soil is applied to vinyl test tiles in 500 µL batches. In addition to surfactants, as shown in Table 9, formulations also contain 1.5% Dowanol PnB solvent. Cleaning efficiency is determined by the grey value from RGB color space. Data are shown in Table 9 below. A higher number indicates more whiteness and therefore better cleaning. The results demonstrate that mixtures of cationic and anionic surfactants according to the invention result in improvement in cleaning.

TABLE 9

| Material | Cleaning |
| --- | --- |
| 0.5% C12 Disulfonate | 61 |
| 0.5% C12 Disulfonate/0.3% Barquat* | 92 |
| 0.5% C14 Disulfonate | 60 |
| 0.5% C14 Disulfonate/0.3% Barquat | 90 |
| 1.5% DOWFAX ™ 2A1 | 58 |
| 1.5% LAS | 80 |
| Cleaner A (a common consumer surface cleaning product) | 93 |
| Cleaner B (a common consumer surface cleaning product) | 62 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A composition comprising:
   (a) a first surfactant of formula I:

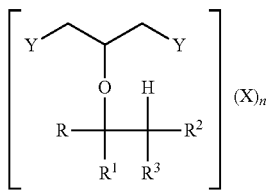

wherein R is linear or branched $C_2$-$C_{22}$ alkyl;
   $R^1$, $R^2$, and $R^3$ are independently H or linear or branched $C_1$-$C_{18}$ alkyl;
   Y is $SO_3^-$ or $N^+R^4R^5R^6$;
   $R^4$, $R^5$, and $R^6$ are independently $C_1$-$C_4$ alkyl, aryl-$C_1$-$C_4$ alkyl, or $R^4$ and $R^5$, together with the nitrogen to which they are attached, form a ring containing 3-9 carbon atoms;
   X is a monovalent or divalent ion;
   n is an integer such that the total ionic charge provided by $X_n$ is 2; and
   (b) a second surfactant that is oppositely charged to the first surfactant.

2. A composition according to claim 1 wherein R is linear $C_4$-$C_{16}$ alkyl.

3. A composition according to claim 1 wherein $R^1$, $R^2$, and $R^3$ are each H.

4. A composition according to claim 1 wherein the total number of carbon atoms in R, $R^1$, $R^2$, $R^3$ and the carbons to which they are attached is 4 to 22.

5. A composition according to claim 1 wherein Y is $SO_3^-$ and X is $H^+$, or a monovalent or divalent cation.

6. A composition according to claim 5 further comprising a compound of the formula IIA:

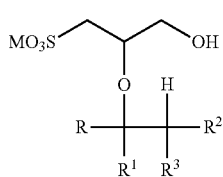

wherein M is $H^+$ or a monovalent or divalent cation, R is linear or branched $C_2$-$C_{22}$ alkyl, and $R^1$, $R^2$, and $R^3$ are independently H or linear or branched $C_1$-$C_{18}$ alkyl.

7. A composition according to claim 1 wherein Y is $N^+R^4R^5R^6$ and X is a monovalent or divalent anion.

8. A composition according to claim 7 wherein $R^4$, $R^5$, and $R^6$ are each methyl.

9. A composition according to claim 1 wherein the second surfactant is hexyltrimethylammonium bromide or chloride, octyltrimethylammonium bromide or chloride, decyltrimethylammonium bromide or chloride, n-dodecyl trimethylammonium bromide or chloride, n-dodecyl ethyldimethylammonium bromide or chloride, tetradecyltrimethylammonium bromide or chloride, tetradecyl ethyldimethylammonium bromide or chloride, n-hexadecyl trimethylammonium bromide or chloride, C4-C16 alkylpyridinium chloride or bromide, dodecyldimethylbenzonium chloride, an alcohol sulfate such as sodium dodecyl sulfate, sodium linear alkylbenzene sulfonate, an alcohol ether sulfate, an alkanesulfonate, an alkyldiphenyloxide disulfonate salt, or a compound of formula IV:

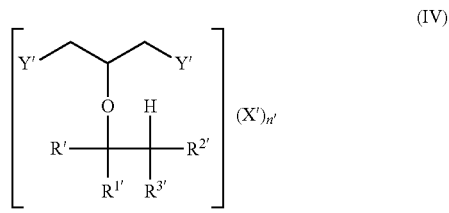

wherein R' is linear or branched $C_2$-$C_{22}$ alkyl; $R^{1'}$, $R^{2'}$, and $R^{3'}$ are independently H or linear or branched $C_1$-$C_{18}$ alkyl; Y' is $SO_3^-$ or $N^+R^{4'}R^{5'}R^{6'}$; $R^{4'}$, $R^{5'}$, and $R^{6'}$ are independently $C_1$-$C_4$ alkyl, aryl-$C_1$-$C_4$ alkyl, or $R^{4'}$ and $R^{5'}$, together with the nitrogen to which they are attached, form a ring containing 3-9 carbon atoms; X' is a monovalent or divalent ion; and n' is an integer such that the total ionic charge provided by $X'_{n'}$ is 2.

10. A composition according to claim 9 wherein the first surfactant is a compound of formula I in which Y is $SO_3^-$ and the second surfactant is a compound of formula IV in which Y' is $N^+R^{4'}R^{5'}R^{6'}$.

11. A composition according to claim 1 wherein the weight ratio of the first surfactant to the second surfactant is from 1:99 to 99:1.

12. A composition according to claim 1 wherein the weight ratio of the first surfactant to the second surfactant is from 40:60 to 60:40.

13. A formulation selected from an agrochemicals formulation, a cleaning formulation, an emulsion polymerization formulation, a paint or coating, a formulation for use in pulp and paper processing, a formulation for use in textile processing, a formulation for use in personal care applications, a formulation for use in oilfield applications, and a water treatment formulation, comprising a composition according to claim 1.

* * * * *